United States Patent [19]

Aebischer et al.

[11] Patent Number: 5,011,472
[45] Date of Patent: Apr. 30, 1991

[54] IMPLANTABLE DELIVERY SYSTEM FOR BIOLOGICAL FACTORS

[75] Inventors: Patrick Aebischer; Pierre M. Galletti, both of Providence; George Panol, Warwick, all of R.I.; Luigi Miracoli, Genoa, Italy

[73] Assignee: Brown University Research Foundation, Providence, R.I.

[21] Appl. No.: 240,939

[22] Filed: Oct. 6, 1988

[51] Int. Cl.⁵ .......................................... A61M 31/00
[52] U.S. Cl. ............................................ 604/50; 604/4; 604/52; 604/53; 604/153; 604/246; 604/892.1
[58] Field of Search ............... 604/50, 52, 53, 153, 604/246, 890.1, 891.1, 892.1, 6, 5, 4; 623/12

[56] References Cited

U.S. PATENT DOCUMENTS

| | | | |
|---|---|---|---|
| 3,093,831 | 6/1963 | Jordan | 623/12 |
| 4,242,459 | 12/1980 | Chick et al. | 435/283 |
| 4,265,241 | 5/1981 | Portner et al. | 128/260 |
| 4,360,019 | 11/1982 | Portner et al. | 128/213 |
| 4,373,527 | 2/1983 | Fischell | 128/260 |
| 4,378,016 | 3/1983 | Loeb | 128/260 |
| 4,391,909 | 7/1983 | Lim | 435/178 |
| 4,395,259 | 7/1983 | Prestele et al. | 604/67 |
| 4,402,694 | 9/1983 | Ash et al. | 604/891 |
| 4,437,815 | 3/1984 | McMullen | 417/418 |
| 4,526,569 | 7/1985 | Bernardi | 604/4 |
| 4,633,878 | 1/1987 | Bombardieri | 128/635 |
| 4,657,490 | 4/1987 | Abbott | 417/478 |
| 4,673,391 | 6/1987 | Kondo et al. | 604/141 |
| 4,687,423 | 8/1987 | Maget et al. | 417/379 |
| 4,705,503 | 11/1987 | Dorman et al. | 604/50 |
| 4,813,951 | 3/1989 | Cannon | 604/891.1 |
| 4,828,543 | 5/1989 | Weiss et al. | 604/6 |
| 4,871,360 | 10/1989 | Theeuwes | 604/892.1 |
| 4,892,538 | 1/1990 | Aebischer et al. | 128/898 |

FOREIGN PATENT DOCUMENTS

| | | |
|---|---|---|
| 0209677 | 1/1987 | European Pat. Off. . |
| 1479002 | 7/1977 | United Kingdom | 623/12 |
| 2131496 | 6/1984 | United Kingdom . |

Primary Examiner—Randall L. Green
Assistant Examiner—Stephanie L. Iantorno
Attorney, Agent, or Firm—Thomas J. Engellener

[57] ABSTRACT

Devices and methods are disclosed to provide hybrid, modular systems for the constitutive delivery of appropriate dosages of active factor to a subject and, in some instances, to specific anatomical regions of the subject. The systems include a cell reservoir containing living cells capable of secreting an active agent, which is preferably adapted for implantation within the body of the subject and further includes at least one semipermeable membrane, whereby the transplanted cells can be nourished by nutrients transported across the membrane while at the same time protected from immunological, bacterial, and viral assault. The systems further include a pumping means, which can be implantable or extracorporeal, for drawing a body fluid from the subject into the cell reservoir and for actively transporting the secreted biological factors from the cell reservoir to a selected region of the subject.

12 Claims, 3 Drawing Sheets

IMPLANTABLE DELIVERY SYSTEM FOR BIOLOGICAL FACTORS

BACKGROUND OF THE INVENTION

The technical field of this invention is devices and methods useful for the treatment of diseases characterized by the deficiency or lack of essential biologically active molecules and, in particular, implantable and extracorporeal devices for the constitutive delivery of such molecules.

Many diseases or conditions of the body are the result of deficiencies in biologically active molecules or factors, such as enzymes, hormones, neurotransmitters, growth factors, and lymphokines which are normally produced by living cells and which are critical in affecting a requisite change in a target tissue or region of the body. Such diseases and conditions include hypoparathyroidism, immune deficiency syndromes, diabetes mellitus, myxedema, Parkinson's disease, and slow bone growth and mending.

One possible remedy for such deficiency diseases is the direct administration of the deficient molecule to the subject. For example, diabetes mellitus has been treated by the administration of insulin. Similarly, the clinical symptoms of Parkinson's disease, a condition characterized by a deficiency of the neurotransmitter, dopamine, have been improved by the systemic administration of the precursors or agonists of dopamine. See, Calne et al. Lancet ii:973-976 (1969) and Calne et al. Bri, Med. J. 4:442-444 (1974). Moreover, treatment of patients having Acquired Immune Deficiency Syndrome with synthetic thymic hormone (TP5) or with thymosin fraction 5 has been reported to lead to the recovery of T lymphocytes proliferation and function, as well as transient clinical improvement. See, Mascart-Lemone et al. Lancet ii:735-736 (1984) and Rubenstein et al. J. Ped. 103:422-427 (1986).

For this type of treatment, systemic administration by bolus injection is the most common mode of administration. Other techniques include the implantation of slow-release capsules containing the factor as disclosed in U.S. Pat. No. 4,324,683 and continuous administration by pumping mechanisms, such as disclosed in U.S. Pat. Nos. 4,373,527; 4,360,019; and 4,395,259).

However, the identification of the deficiency and the synthesis or isolation of the factor in a form which is stable, pure, and biologically active can be expensive, time-consuming, and difficult. In addition, other problems may be encountered pertaining to determining the appropriate dosage and mode of administration. Also, the recoveries decline upon cessation of the treatment, necessitating long-term, continuous therapy.

An alternative mode of therapy has been to augment or replace the absent or dysfunctional tissue with viable tissue capable of providing the necessary factor. However, prior attempts to do so in a variety of deficiency disorders have often proven to be unsuccessful because of immune reactions (in cases where foreign tissue was utilized) or microbial assault. One solution to this problem disclosed, for example, in U.S. Pat. Nos. 4,391,909 and 3,093,831, has been to encapsulate the factor-producing cells within protective membranes which allow the free diffusion of active factor and nutrients while excluding hostile elements from passage. However, once placed in the body, these encapsulated cells can have a limited life span. Artificial implantable glands with replaceable or replenishable cell cultures have also been developed to solve this problem (as disclosed in U.S. Pat. Nos. 4,242,459; 4,402,694; and 4,378,016), but such devices often have been sluggish in delivering the needed biological factors.

There exists a need for improved therapies for diseases characterized by a deficiency in an active factor in general, and in particular, a need for systems which can augment or replace the functions of dysfunctional glands or tissues of the body. More specifically, there exists a need for a method of providing an active factor to a localized region of the body of a subject deficient or requiring this factor, the correct dosage of which will be constitutively and expeditiously delivered over time.

Accordingly, it is an object of the present invention to provide devices and methods for delivering an active factor to a subject deficient in or in need of that factor and to provide methods of delivering such a factor safely and expeditiously to a localized region of the body of that subject. It is another object of the present invention to provide devices for, and methods of, delivering active factors quickly and in a manner constitutively responsive to the internal environmental requirements of the subject. It is yet another object of the invention to provide an active factor to a subject, the source of which is relatively small, compact, and which requires little surgical maintenance. A further object of the invention is to provide cell culture devices which protect the cells therein from immunological, bacterial, and viral assault, while allowing the delivery of an active factor therefrom.

SUMMARY OF THE INVENTION

Devices and methods are disclosed to provide hybrid, modular systems for the constitutive delivery of appropriate dosages of active factors to a subject and, in some instances, to specific anatomical regions of the subject. The systems provide means for convective transport of active factors to the subject and thereby lessen the problem of response time typically associated with implanted, diffusion-type drug dispensers and encapsulated tissue transplants.

The systems, according to the present invention, include a cell reservoir containing living cells capable of secreting an active agent. The cell reservoir is preferably adapted for implantation within the body of a subject, which can be human or animal, and further includes at least one semipermeable membrane, whereby the transplanted cells can be nourished by nutrients transported across the membrane while at the same time protected from immunological, bacterial, and viral assault.

The systems of the present invention further include a pumping means, which can be implantable or extracorporeal, for drawing a body fluid from the subject into the cell reservoir and for actively transporting the secreted biological factors from the cell reservoir to a selected region of the subject. The body fluid can be interstitial fluid, lymph fluid, ascites fluid, cerebral spinal fluid, plasma, or serum.

The term "active factor" is used herein to describe a desired therapeutic, biologically active molecule, such as a drug, enzyme, hormone, growth factor, neurotransmitter, lymphokine, interferon, colony stimulating factor, plasminogen activator, tumor recrosisfactor, or other cytokine, or active fragment, analog, or derivative thereof, which is secreted by a living cell.

The cell reservoirs of the present invention are preferably constructed to house from about $10^4$ to about $10^9$ cells, depending on the disease to be treated and the efficiency of the cells in producing the desired active factor(s). The metabolic synthesis and secretion of active factors by the cells serves not only to provide a self-replenishing source of the therapeutic factors, but also avoids the so-called "time-bomb" risk of inadvertent release of overdose amounts of a factor, a problem that is otherwise inherent in drug delivery devices which are filled with a long-term supply of the therapeutic agent.

The term "semipermeable" is used herein to describe biocompatible membranes which are permeable to solutes having a molecular weight of up to about 100,000 daltons and preferably of up to about 50,000 daltons. Membranes useful in defining the cell reservoirs of the present invention for cell encapsulation can be tubular and can, for example, be composed of at least one material selected from the group consisting of acrylic copolymers, polyurethane isocyanates, cellulose acetate, polyalginate, polysulfone, polyvinyl alcohols, polyvinylidene fluoride, polyacryl nitriles, derivatives, and mixtures thereof.

The pumping means of the present invention can be mechanical, electromechanical, piezoelectric or thermodynamic. In one illustrated embodiment, the pumping action is produced by a solenoid-driven piston which serves to draw a body fluid into the cell reservoir and from there into a delivery catheter. By actively pumping to create a convective flow of the active factors to the subject rather than relying on diffusion across the semipermeable membrane alone, the present invention overcomes a significant disadvantage of prior art artificial organ systems, that being the rate limitation inherent in diffusion.

Moreover, the pumping action also provides a mechanism for immediate natural biofeedback control of the delivery rate of the active factors, at least when the implanted cells exhibit self-regulatory behavior. Thus, if the subject returns to a roughly normal physiologically state, the convective flow of body fluid through the cell reservoir permits the implanted cells to sense and respond to this situation by reducing their secretion of the active factor and, conversely, if the subject's condition again becomes unbalanced, as evidenced by changes in the composition of the body fluids drawn through the cell reservoir, the cells can be stimulated to produce greater quantities of the active factors.

Additionally, the system of the present invention can include a catheter coupled to, and in fluid communication with, the pumping means to transport the active factor to a selected region of the subject. This feature is particularly advantageous in situations where it is necessary to overcome a fundamental biological obstacle, such as intracerebral delivery of drugs and other biological substances which would not otherwise be able to cross the blood-brain barrier. This feature is especially important in the delivery of dopamine or other neurotransmitters to the brain for the treatment of Parkinson's disease and similar disorders. The catheter can include a biocompatible coating, such as high density, turbostratic carbon.

The delivery system can further include a controller electronically coupled to the pumping means to control fluid transport through the pump, and it can also include a back-up supply cartridge containing the active factor. In one embodiment, the back-up supply cartridge is also in fluid communication with the pumping means and responsive thereto for delivery of the active factor to a selected region of said subject in the event that the cell reservoir is disabled. Both the controller and the back-up cartridge (or portions thereon) can be extracorporeal or implanted.

Methods are also disclosed for delivering an active factor to a selected region in a subject. The methods include the steps of providing a cell reservoir and pumping means which cooperate to deliver an active factor to the subject. In the methods of the present invention, the pumping means provides a convective flow of body fluid from the subject to the cell reservoir and back to the subject, supplemented with an active factor secreted by implanted cells within the reservoir.

The methods of the present invention can further include the step of providing a controller electronically coupled to the pumping means to control the flow of fluid therethrough. The method can also include the step of providing a back-up supply cartridge for delivery of the active factor to the subject in the event that the biological source is disabled or depleted.

The invention will next be described in connection with certain illustrated embodiments. However, it should be clear that various modifications, additions, and subtractions can be made without departing from the spirit or scope of the invention.

BRIEF DESCRIPTION OF THE DRAWINGS

The foregoing and other objects of the invention and the various features thereof, as well as the invention itself, may be more fully understood from the following description when read together with the accompanying drawings in which.

DETAILED DESCRIPTION

Figure 1:
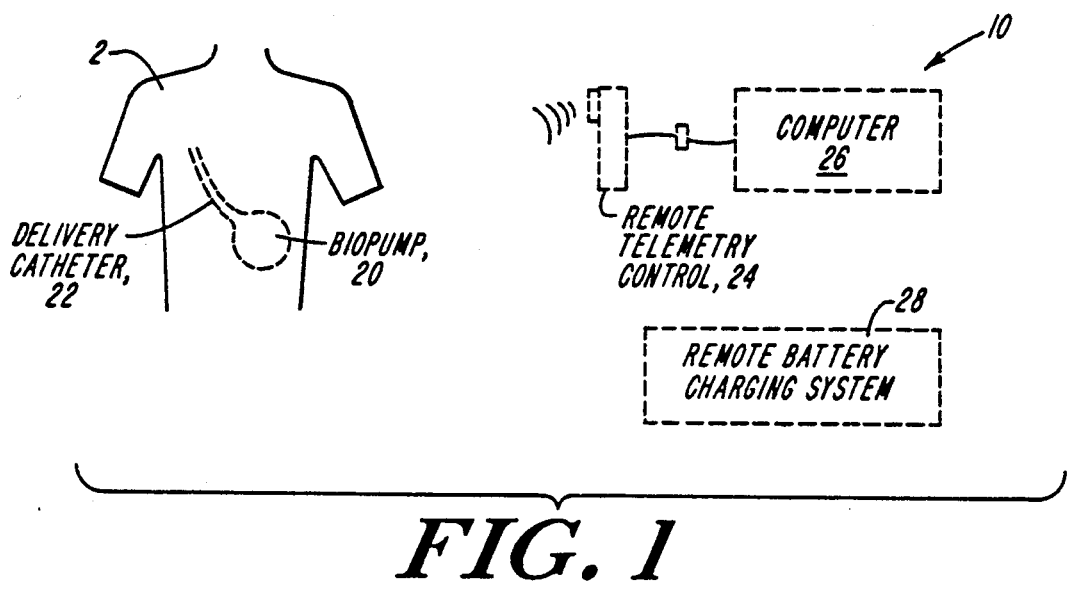
FIG. 1 is an overall schematic diagram of an implantable delivery system for biological factors according to the present invention.

FIG. 1 provides an overall schematic diagram of a delivery system 10 according to the present invention, including a biopump 20 and biocompatible delivery catheter 22, both disposed within a subject 2. The biopump 20 and delivery catheter 22 cooperate to generate in vivo a desired therapeutic, biologically-active factor, such as a drug, hormone, neurotransmitter, lymphokine, etc., and to deliver such therapeutic factor to a target region within the subject 2. The target region can be any part of the anatomy of the subject which responds to the active factor, or which requires the factor for normal function. The biopump 20 can be controlled by an external computer 26 via signals transmitted by a remote telemetry control 24. As shown, the biopump 20 can also include a rechargeable battery which is periodically charged by remote battery charging system 28.

Figure 2:
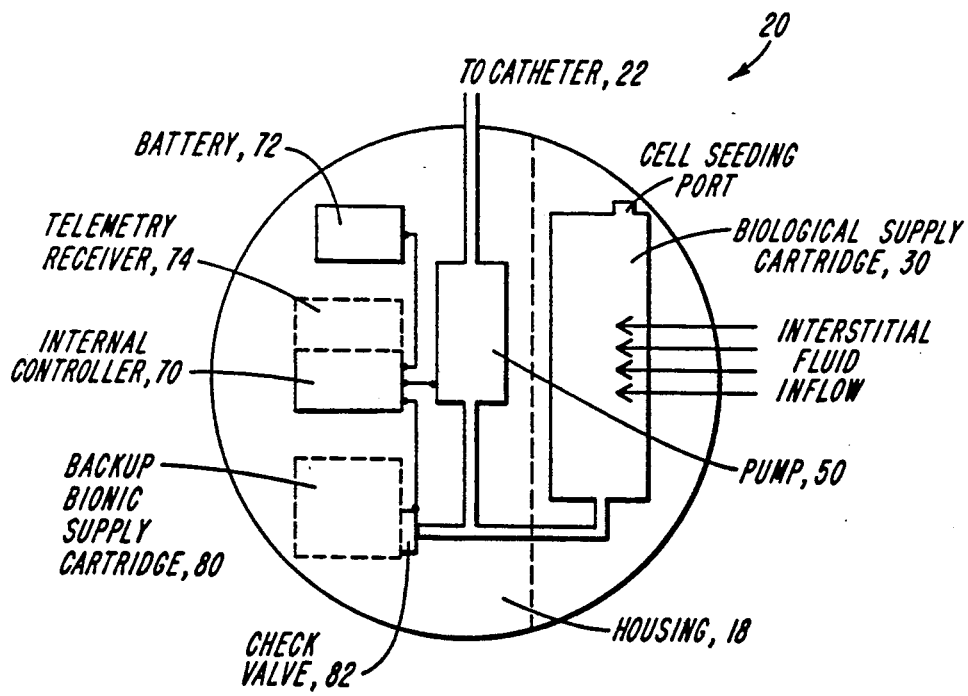
FIG. 2 is a more detailed schematic diagram of the implantable delivery system of FIG. 1.

In FIG. 2, the biopump 20 is shown in more detail, including a biological supply cartridge 30, pump 50, internal controller 70 (which can include a pre-programmed microprocessor) and battery 72. As shown, the controller can also include an optional telemetry receiver 74 to receive remote telemetry controls (as shown in FIG. 1). Additionally, the biopump 20 can include a back-up, bionic supply cartridge 80 and check valve 82, activatable by controller 70, in the event that the biological supply cartridge 30 is depleted or disabled.

Under normal operating conditions, the biological supply cartridge 30 is populated with cells capable of secreting an active factor. The pump 50 cooperates with the cartridge 30 to transfer such factor to the subject. The biopump 20 is preferably constructed for implantation, such that at least the biological supply cartridge (or a portion thereof) is exposed to the subject's tissue to extract a body fluid during operation of the system. Alternatively, at least part of the biopump 20 can be worn extracorporeally but connected to the patient to extract and return a body fluid. In either case, the body fluid from the subject is drawn into and through the cartridge 30, carrying with it the active factor secreted by the cells within the cartridge. The factor-laden fluid is then pumped by pump 50 into catheter 22 for delivery to a target region within the subject. The catheter 22 can be coated with a material, such as turbostratic carbon or the like, to render it biocompatible with the subject.

Figure 3A:
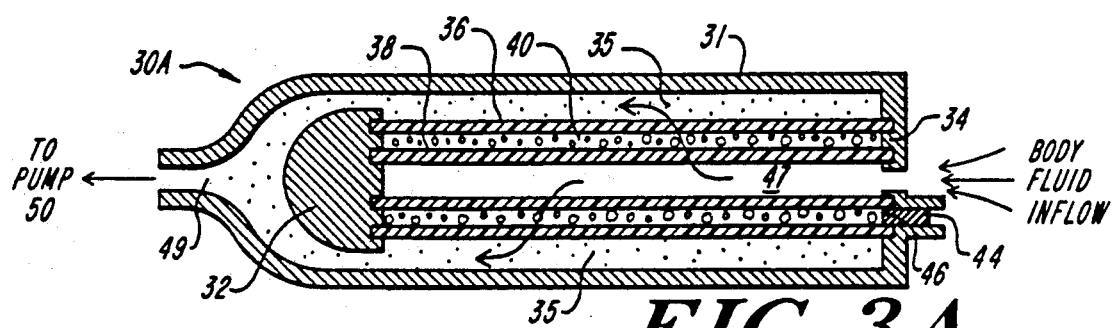
FIG. 3A and 3B are cross-sectional schematic diagrams of alternative embodiments of the biological supply cartridge of FIG. 2.

In FIG. 3A, a more detailed schematic illustration of one embodiment of the biological supply cartridge 30A of FIG. 2 is presented, including housing 31 (which can also be used to mount the biological supply cartridge to the biopump housing 18 shown in FIG. 2); an inner cavity 47 in fluid communication with the subject; an inner, tubular, semipermeable membrane 38 partially surrounding cavity 47, and an outer, tubular, semipermeable membrane 36. The membranes 36 and 38 are secured in concentric configuration by end cap 32 and end wall 34 of the housing 31.

The inner and outer membranes 36, 38 define therebetween a cell reservoir 40 which is populated with cells 42. The cartridge 30A includes a cell seeding port 44 sealed by septum 46 for initially seeding and subsequently replenishing, if necessary, the cell reservoir 40. On the outside of outer membrane 38 and surrounding cell reservoir 40 is a collecting chamber 35 which is connected to pump 50 by outlet 49. During operation, body fluid is drawn into inner cavity 47 and through inner semipermeable membrane 36 into reservoir 40. The fluid and active factors secreted by the cells are then further drawn from reservoir 40 through outer semipermeable membrane 36 into collecting member 35 and out of cartridge 30A through port 49 to pump 50.

Figure 3B:
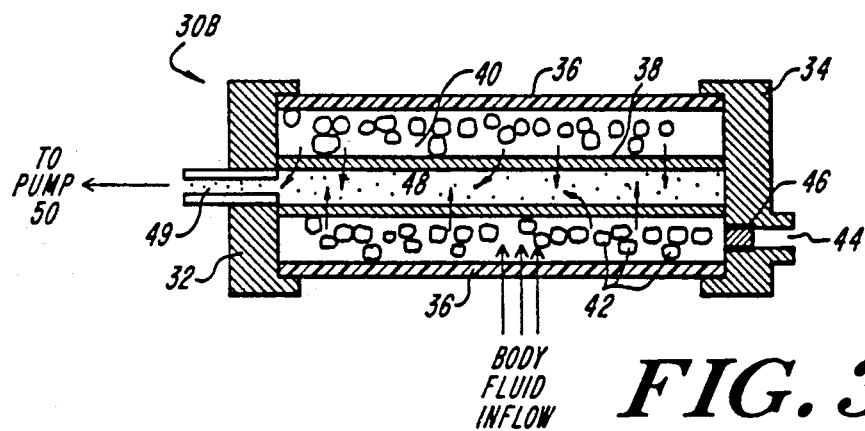

An alternative embodiment of a biological supply cartridge 30B according to the invention is depicted in FIG. 3B. It includes first and second end caps 32 and 34 (which again can be used to mount the biological supply cartridge to the pump housing 18 shown in FIG. 2), an outer, tubular, semipermeable membrane 36 and an inner, tubular, semipermeable membrane 38. As in FIG. 3A, the inner and outer membranes 36, 38 define therebetween a cell reservoir 40 which is populated with cells 42. The cartridge 30B also includes a cell seeding port 44 sealed by septum 46 for initially seeding and subsequently replenishing, if necessary, the cell reservoir 40.

Biological supply cartridge 30B of FIG. 3B includes an internal cavity 48 which is connected to pump 50 by outlet 49. In this embodiment, the subject's body fluid is drawn through outer, semipermeable membrane 36 into reservoir 40. As it travels through the reservoir 40, the fluid contacts and entrains active factors which pass with it through the inner semiPermeable membrane 38 and into internal cavity 48 in response to the action of pump 50.

The biological supply cartridges of FIGS. 3A and 3B can be populated by a variety of cells, depending upon the desired therapeutic or active factor. Typically, the size of the cell population in the supply cartridges will range from about $10^4$ to $10^9$ cells. They can be homografts or allografts, including fetal cells, established cell lines, or cells from donors of the same species, or they can be xenografts from another species. They can be derived from a body organ which normally secretes a particular active factor in vivo or, more generally, any cell which secretes an active factor, such as a neurotransmitter, enzyme, hormone, or a precursor, analog, derivative, agonist or fragment thereof having similar activity can be used.

Moreover, cells which have been genetically engineered to express an active factor or precursor, derivative, analog, or fragment thereof having similar activity are also useful in practicing this invention. Briefly, in such an approach, the gene which encodes the therapeutic factor or its derivative, analog, or precursor, is either isolated from a cell line or constructed by DNA manipulation.

The gene can then be incorporated into a plasmid, which, in turn, is transfected into a set of cells for expression. The cells which express the active factor can be grown in vitro until a suitable density is achieved. A portion of the culture can then be used to seed the implantable device. (See, e.g., Maniatis et al., *Molecular Cloning* (1982), herein incorporated by reference for further discussion of cloning vehicles and gene manipulation procedures.)

The semipermeable membranes 36 and 38 which define reservoir 40 serve to protect the cells from deleterious encounters with viruses and elements of the subject's immune system. Such protection is particularly important for preserving allografts or xenografts which are foreign to the body, and could otherwise elicit an immune response. Preferably, the membrane should exclude the passage of viruses, macrophages, complement, lymphocytes, and antibodies therethrough, while allowing the diffusion of nutrients, gases, metabolic breakdown products, other solutes, and the active factor. Accordingly, any biocompatible and nonresorbable materials having pores enabling the diffusion of molecules having a molecular weight of up to about 50,000 daltons are useful for practicing the present invention with acrylic copolymers, polyvinylidene fluoride, polyurethane isocyanates polyalginate, cellulose acetate, polysulfone, polyvinyl alcohols, polyacrylonitrile, derivatives, and mixtures thereof being the most preferable.

Further descriptions of membranes materials for cell encapsulation, as well as techniques for cell culturing and implantation, can be found in commonly-owned, copending U.S. Pat. applications Serial No. 090,448 "Apparatus And Methods Of Immunotherapy With Encapsulated Thymic Cells" by Aebischer et al. filed Aug. 28, 1987, and Ser. No. 121,626 "In Vivo Delivery of Neurotransmitters By Implanted Encapsulated Cells" by Aebischer et al. filed Nov. 17, 1987, both of which are incorporated herein by reference.

Figure 4:
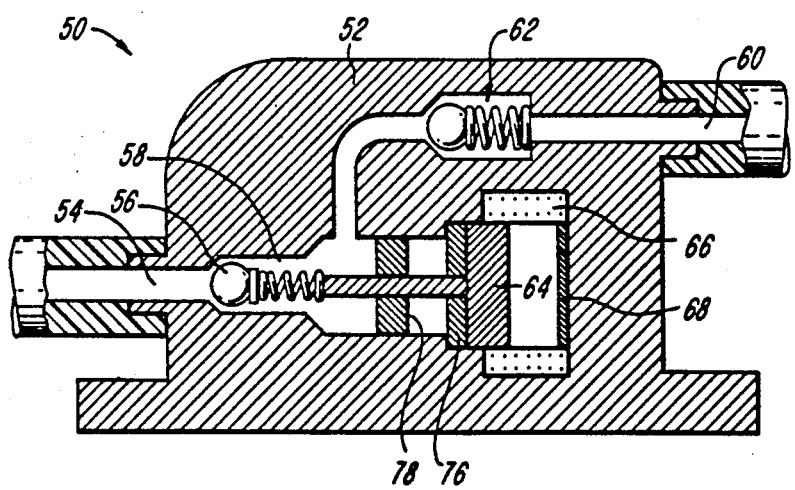
FIG. 4 is a cross-sectional schematic diagram of the pump element of FIG. 2.

FIG. 4 is a more detailed schematic illustration of pump 50, including a pump casing 52 having an inlet 54, held in a normally closed position by inlet check valve 56 (which can be, for example, a spring-loaded ball valve), an internal chamber 58, and an outlet 60, again, normally closed by outlet check valve 62. Also disposed within the casing 52 is a cylindrical solenoid 66 and reciprocating piston 64. Upon activation of the solenoid 66, piston 64 is drawn to end plate 68 and the inlet valve 56 is opened. Permanent magnet 76 can also be disposed within the casing to attract the piston 64 when solenoid 66 is not activated and thereby close valve 56. Shaft seal 78 can be disposed to isolate the piston from the pump chamber 58. In operation, the reciprocating motion of the piston 64 creates a negative pressure in the pump chamber causing both the inlet and outlet valves 56 62 to open and thereby transfer fluid from inlet 54 to outlet 60.

Figure 5:
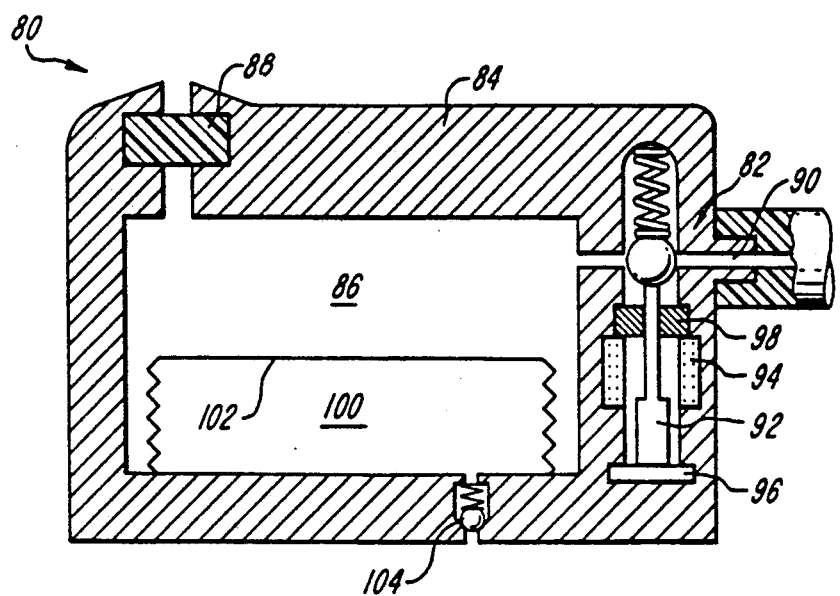
FIG. 5 is a cross-sectional schematic diagram of the back-up bionics supply cartridge of FIG. 2.

FIG. 5 is a more detailed schematic illustration of a back-up bionic supPly cartridge 80 and check valve 82. The supply cartridge 80 includes a casing 84 and an internal drug supply chamber 86, which can be filled and replenished by septum seal inlet 88. The check valve includes a cylindrical solenoid 94 and a piston 92 disposed for reciprocal motion in and out of the solenoid core. Piston 92 is connected to a ball valve which controls the fluid passageway from chamber 86 to outlet 90. During periods of non-use, piston 92 is drawn to permanent magnet 96 such that the ball valve is closed. Upon activation of the solenoid coil 94 to open the ball valve, piston 92 is drawn into the core of the solenoid 94, and the valve is opened. In order to compensate for negative pressure which builds up in the drug supply chamber upon use, a compensation chamber 100 is also disposed within the casing 84. The volume of the compensation chamber can expand by movement of bellows 102 and the inflow of interstitial fluid via check valve 104.

The device 20 as shown in FIG. 1 can be surgically implanted into the peritoneum or any accommodating body cavity as a whole or in part. For example, the cell cartridge 30 can be implanted first so as to determine the amount of active factor which is secreted and which is required for corrective therapy. If for any reason a problem is encountered with the cell cartridge 30, the back-up supply cartridge 80 can be connected. In this way, the delivery system can be conveniently maintained.

The delivery systems of the present invention (or various components) have been tested in vitro and in animal models. In particular, various semipermeable membrane materials have been employed to culture cells, including thymic cells, secreting various lymphocyte maturation factors, and adrenal cells, secreting dopamine or other neurotransmitters. In vitro studies employing a roller pump and a double walled cell compartment bathed in a nutrient medium demonstrated that the medium can be pumped through the cell reservoir to extract biological agents secreted by the cells (i.e., T-cell growth factors secreted by encapsulated thymic epithelial cells).

In an in vivo study on mice, kidney ephithelial cells were seeded in a biological supply cartridge having a double walled construction of semipermeable acrylic copolymer tubes. The cells were grown to confluence, and the cartridge was then implanted into the peritoneal cavity of the animal. A peristaltic pump (Ismatek Model 7619-40) was also implanted and connected to the cell reservoir by silicone tubing to draw the animal's body fluids through the cell reservoir. Flow rates of 0.01 ml per minute were demonstrated with the implants exhibiting good patency. The fluids withdrawn by the pump were analyzed and found to include various factors secreted by the transplanted kidney cells.

What is claimed is:

1. A delivery device for delivering a biologically active factor to a subject, the device comprising: a cell reservoir means for receiving at least one active, factor-secreting cell, said means including a chamber having at least one semipermeable membrane, said membrane adapted to be held in contact with a source of body fluid for introducing body fluid into said reservoir means; and pumping means for transporting a secreted active factor from said reservoir means to a selected region in a subject, whereby at least one active, factor-secreting cell is located within said reservoir means for secreting an active factor, which active factor is carried to said selected region via body fluid introduced into said reservoir through said membrane.

2. The device of claim 1 wherein at least a portion of the device is adapted for implantation within the subject, and the pumping means further includes means for convectively drawing a body fluid from the subject into the cell reservoir.

3. The device of claim 1 wherein said semipermeable membrane of said cell reservoir is a tubular membrane.

4. The device of claim 1 wherein said semipermeable membrane of said cell reservoir is a material selected from the group consisting of acrylic copolymers, polyurethane isocyanates, cellulose acetate, polyalginate, polysulfone, polyvinyl alcohols, polyvinylidene fluoride, polyacryl nitriles, and derivatives and mixtures thereof.

5. The device of claim 1 wherein said semipermeable membrane of said cell reservoir is a porous material, allowing the passage therethrough of molecules with a molecular weight of up to about 100,000 daltons.

6. The device of claim 1 wherein said semipermeable membrane of said cell reservoir is a porous material allowing the passage therethrough of molecules with a molecular weight of up to about 50,000 daltons.

7. The device of claim 1 wherein the device further includes a catheter connected to said pumping means and in fluid communication therewith to transport said active factor to said selected region in said patient.

8. The device of claim 7 wherein the catheter further includes a biocompatible coating.

9. The device of claim 8 wherein the catheter further includes a biocompatible turbostratic carbon coating.

10. The device of claim 1 wherein the device further includes a controller electronically coupled to said pumping means to control fluid transport through said pumping means.

11. The device of claim 1 wherein said device further includes a back-up supply cartridge containing said active factor, said back-up supply cartridge being in fluid communication with said pumping means, and responsive thereto for delivery of said active factor to said selected region of said subject.

12. A delivery device for delivering a biologically active factor to a selected region in a living subject, the device comprising:

a cell reservoir means for receiving at least one active, factor-secreting cell, including a chamber having at least one semipermeable membrane, said membrane comprising means for permeation into said reservoir means of selected body fluid from a source of body fluid and means for permeation of a portion of said selected body fluid out of said reservoir along with an active factor secreted by said at least one cell, and pump means for transporting said selected body fluid, whereby at least one active, factor-secreting cell is located within said reservoir means for secreting an active factor, which active factor is transported by said transported selected body fluid for delivery to a selected region in the living subject.

* * * * *